United States Patent
Eder

(10) Patent No.: US 6,743,251 B1
(45) Date of Patent: Jun. 1, 2004

(54) IMPLANTABLE DEVICES WITH POLYMERIC DETACHMENT JUNCTION

(75) Inventor: Joseph C. Eder, Los Altos Hills, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/714,038

(22) Filed: Nov. 15, 2000

(51) Int. Cl.[7] .................................................. A61F 2/06
(52) U.S. Cl. ........................................ 623/1.11; 606/200
(58) Field of Search ............................. 623/1.11–1.16; 606/151, 191, 108, 195, 32, 200; 600/585

(56) References Cited

U.S. PATENT DOCUMENTS

| | | |
|---|---|---|
| 4,655,771 A | 4/1987 | Wallstén |
| 4,735,201 A | 4/1988 | O'Reilly |
| 4,954,126 A | 9/1990 | Wallsten |
| 4,994,069 A | 2/1991 | Ritchart et al. |
| 5,061,275 A | 10/1991 | Wallsten et al. |
| 5,108,408 A | 4/1992 | Lally |
| 5,122,136 A | 6/1992 | Guglielmi et al. |
| 5,234,437 A | 8/1993 | Sepetka |
| 5,250,071 A | 10/1993 | Palermo |
| 5,261,916 A | 11/1993 | Engelson |
| 5,304,195 A | 4/1994 | Twyford, Jr. et al. |
| 5,312,415 A | 5/1994 | Palermo |
| 5,350,397 A | 9/1994 | Palermo et al. |
| 5,423,829 A | 6/1995 | Pham et al. |
| 5,522,836 A | 6/1996 | Palermo |
| 5,569,245 A * | 10/1996 | Guglielmi et al. ............ 606/49 |
| 5,624,461 A | 4/1997 | Mariant |
| 5,639,277 A | 6/1997 | Mariant et al. |
| 5,649,949 A | 7/1997 | Wallace et al. |
| 5,722,979 A * | 3/1998 | Kusleika ...................... 604/22 |
| 5,759,161 A | 6/1998 | Ogawa et al. |
| 5,846,210 A | 12/1998 | Ogawa et al. |
| 5,944,733 A | 8/1999 | Engelson |
| 6,059,779 A * | 5/2000 | Mills .......................... 600/373 |
| 6,059,815 A * | 5/2000 | Lee et al. .................... 606/209 |
| 6,063,111 A * | 5/2000 | Hieshima et al. .......... 623/1.11 |
| 6,102,917 A * | 8/2000 | Maitland et al. ............ 606/108 |
| 6,168,570 B1 * | 1/2001 | Ferrera ........................ 600/585 |
| 6,296,622 B1 * | 10/2001 | Kurz et al. ............... 604/93.01 |
| 6,346,091 B1 * | 2/2002 | Jacobsen et al. .............. 604/57 |
| 6,370,757 B2 * | 4/2002 | Lee et al. ...................... 29/447 |
| 6,458,119 B1 * | 10/2002 | Berenstein et al. ............ 606/1 |

FOREIGN PATENT DOCUMENTS

| | | |
|---|---|---|
| EP | 0 739 607 | 10/1996 |
| EP | 0 992 220 | 4/2000 |
| JP | 7-265431 | 10/1995 |
| WO | WO 99/02094 | 1/1999 |
| WO | WO 00/48517 | 8/2000 |
| WO | WO 00/54832 | 9/2000 |
| WO | WO 00/72781 | 12/2000 |

* cited by examiner

*Primary Examiner*—Michael J. Milano
*Assistant Examiner*—(Jackie) Tan-Uyen T. Ho
(74) *Attorney, Agent, or Firm*—Robins & Pasternak LLP

(57) ABSTRACT

Disclosed herein are implantable devices, such as vaso-occlusive coils and stents, comprising a junction member linking the device to a delivery mechanism. The junction member is melted or severed from the implantable using low frequency energy or direct current (DC).

12 Claims, 1 Drawing Sheet

IMPLANTABLE DEVICES WITH POLYMERIC DETACHMENT JUNCTION

FIELD OF THE INVENTION

This invention relates to the field of implantable devices. More particularly, it relates to detaching the implantable device from the delivery mechanism using low frequency energy or direct current (DC) to melt or sever the polymeric junction between the device and delivery mechanism.

BACKGROUND

There are a variety of implantable devices that require precise placement within the vasculature of the human body. Such devices include vaso-occlusive coils, stents and other three-dimensional devices. Vaso-occlusive coils are described, for example, in U.S. Pat. No. 4,994,069, to Ritchart et al.; U.S. Pat. No. 5,624,461 to Mariant; U.S. Pat. No. 5,639,277 to Mariant et al. and U.S. Pat. No. 5,649,949 to Wallace et al. describes variable cross-section conical vaso-occlusive coils. Stents are described, for example, in U.S. Pat. No. 4,655,771 to Wallsten; U.S. Pat. No. 4,954,126 to Wallsten and U.S. Pat. No. 5,061,275 to Wallsten et al.

Typically, implantable devices include a detachment mechanism in order to be released from the deployment mechanism (e.g., attached wire). Several classes of techniques have been developed to enable more accurate placement of implantable devices within a vessel. One class involves the use of electrolytic means to detach the vasoocclusive member from the pusher. In one technique (U.S. Pat. No. 5,122,136 to Guglielmi et al.) the vasoocclusive member is bonded via a metal-to-metal joint to the distal end of the pusher. The pusher and vasoocclusive member are made of dissimilar metals. The vasoocclusive member-carrying pusher is advanced through the catheter to the site and a low electrical current is passed through the pusher-vasoocclusive member assembly. The current causes the joint between the pusher and the vasoocclusive member to be severed via electrolysis. The pusher may then be retracted leaving the detached vasoocclusive member at an exact position within the vessel. In addition to enabling more accurate vasoocclusive member placement, the electric current may facilitate thrombus formation at the vasoocclusive member site. The only perceived disadvantage of this method is that the electrolytic release of the vasoocclusive member requires a period of time so that rapid detachment of the vasoocclusive member from the pusher does not occur. Other examples of this technique can be found in U.S. Pat. No. 5,423,829 to Pham et al. and U.S. Pat. No. 5,522,836 to Palermo.

Other forms of energy are also used to sever sacrificial joints that connect pusher and vasoocclusive member apparatus. An example is that shown in Japanese Laid-Open Patent Application No. 7-265431 or corresponding U.S. Pat. No. 5,759,161 and U.S. Pat. No. 5,846,210 to Ogawa et al. A sacrificial connection member, preferably made from polyvinylacetate (PVA), resins, or shape memory alloys, joins a conductive wire to a detention member. Upon heating by a monopolar high frequency current, the sacrificial connection member melts, severing the wire from the detention member. U.S. Pat. 5,944,733 to Engelson describes application of radiofrequency energy to sever a themoplastic joint.

In U.S. Pat. No. 4,735,201 to O'Reilly, an optical fiber is enclosed within a catheter and connected to a metallic tip on its distal end by a layer of hot-melt adhesive. The proximal end of the optical fiber is connected to a laser energy source. When endovascularly introduced into an aneurysm, laser energy is applied to the optical fiber, heating the metallic tip so as to cauterize the immediately surrounding tissue. The layer of hot-melt adhesive serving as the bonding material for the optical fiber and metallic tip is melted during this lasing, but the integrity of the interface is maintained by application of back pressure on the catheter by the physician. When it is apparent that the proper therapeutic effect has been accomplished, another pulse of laser energy is then applied to once again melt the hot-melt adhesive, but upon this reheating the optical fiber and catheter are withdrawn by the physician, leaving the metallic tip in the aneurysm as a permanent plug.

Other methods for placing implantable devices within the vasculature utilize heat releasable bonds that can be detached by using laser energy (see, U.S. Pat. No. 5,108, 407). EP 0 992 220 describes an embolic coil placement system which includes conductive wires running through the delivery member. When these wires generate sufficient heat, they are able to sever the link between the embolic coil and the delivery wires. Further, U.S. Ser. No. 09/177,848 describes the use of fluid pressure (e.g., hydraulics) to detach an embolic coil.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250, 071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vasoocclusive coil assembly having an affixed, proximally extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

None of these documents disclose devices having detachment junctions that are detachable by applying low frequency or direct current.

SUMMARY OF THE INVENTION

The present invention includes compositions and methods for detaching implantable devices from deployment mechanisms using low-frequency energy or direct current.

In one aspect, the invention includes an assembly comprising (a) an implantable device; (b) a deployment mechanism; and (c) a junction member linking the implantable device and deployment mechanism. The junction member is detached from the implantable device by application of low-frequency energy or direct current, for example a thermoplastic polymer such as PVA. In certain embodiments, the low frequency or direct current is less than 100 kHz, preferably less than 80 Hz. The deployment mechanism can comprise, for example, a conductive wire. The implantable device can comprise, for example, a vasoocclusive coil or a stent.

In other aspects, any of the devices and/or assemblies described herein further include a source of low frequency energy or direct current attached to the delivery mechanism and/or a conductive member in operable contact with the junction member. In other embodiments, the assembly devices described herein further comprise a catheter, said assembly being disposed within the catheter. Further, the catheter may include a negative electrode at the distal tip of the catheter.

In other aspects, methods of using the assembly devices are provided, for example introducing an assembly as described herein into a subject and detaching the implantable device in the desired location by applying low frequency energy or direct current.

These and other embodiments of the subject invention will readily occur to those of skill in the art in light of the disclosure herein.

DESCRIPTION OF THE INVENTION

Figure 1:
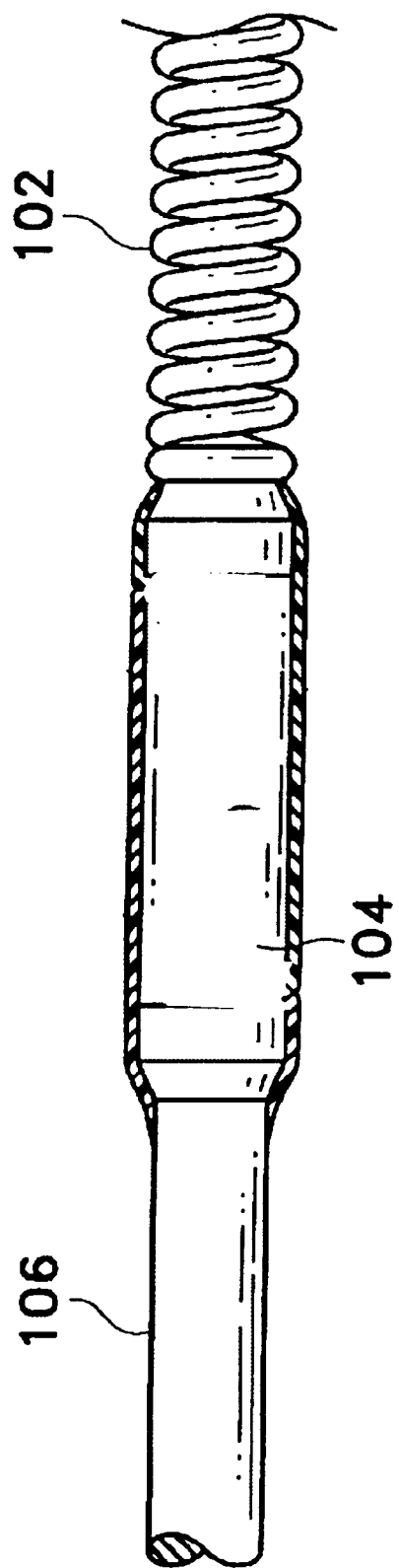
FIG. 1 is a partial sectional view of one example of the an assembly of the present invention with a thermoplastic junction member and an implantable vaso-occlusive coil.

Implantable devices, such as coils or stents, with detachable junctions to delivery mechanisms are described. Thus, the devices include junction members which link the device to the deployment mechanism. The junction members are readily detachable by the imposition of low frequency energy (or direct current) by the operator when the device is in the desired position. Methods of making and using these devices also form an aspect of this invention.

Advantages of the present invention include, but are not limited to, (i) increasing the precision of placement of implantable devices; (ii) decreasing the time needed for separation of implant from delivery mechanism; (iii) providing implant delivery systems that require only one delivery wire; (iii) providing implant delivery systems that can be used with flexible catheters; and (iv) providing methods and materials for making these detachable devices.

All publications, patents and patent applications cited herein, whether supra or infra, are hereby incorporated by reference in their entirety.

It must be noted that, as used in this specification and the appended claims, the singular forms "a", "an", and "the" include plural referents unless the content clearly dictates otherwise. Thus, for example, reference to "a junction member" includes a one or more junction members on a single device.

The low-frequency energy or DC severable junctions described herein can be used in the manufacturing of a wide variety of implantable devices, including but not limited to stents and vaso-occlusive devices such as coils. Other implantable devices will also be advantageously employed with the junctions described herein.

A junction member (104) is fixedly attached to the implant (102) and to the delivery mechanism (e.g., a wire, pusher, etc.) (106). The sites of attachment can be determined based on the use of the implant and the desired final, deployed configuration. Thus, in certain embodiments, the junction member is attached to just one location on both the implant and the delivery mechanism, for example, on or near the proximal end of the implant and on or near the distal end of the delivery mechanism. For purposes of this invention, the term "engaged" is herein used to describe any mechanical or physical attachment, interlocking, mating, binding, coupling, hooking, etc., such that members that are said to be "engaged" do not come apart or detach from one another without some positive effort, application of energy, or the like.

The junction member is preferably a thermoplastic member that melts or sufficiently weakens upon application of low frequency energy or direct current (DC). As will be apparent to those of skill in the art, the junction member need not melt completely in order to be severable from the implantable device. The junction member need only melt sufficiently that the operator can remove the delivery mechanism.

The thermoplastic junction member can be made using any conventional technique, for example by substantially coating the desired cleavage of a junction of implant and delivery mechanism. One technique, for example, is dipping or coating the implant and delivery mechanism in molten or substantially softened thermoplastic material, but other techniques as known in the art, such as shrink-wrapping, spraying on in the form of a suspension or latex, or others may be used as well. Other conventional techniques, such as line of sight spray deposition, may also be used. Once a sufficient thickness of the thermoplastic junction member has been obtained, the implantable device and delivery mechanism are linked via this junction member. In certain instances, the entire surface of implant and/or delivery mechanism is substantially to electrically insulate to limit the heating effect of the energy applied during deployment of implant.

In some embodiments, preferably prior to the passing of time to allow substantial hardening of the thermoplastic material, the junctions are physically engaged to form the delivery assembly prior to insertion of the assembly inside a catheter. The delivery assembly can include implantable member, delivery wire, sleeve, catheter, etc.

No limitation is imposed on the material for the junction member so long as it does not adversely affect the patient's body and can be severed by application of low frequence energy or DC current. Thus, any suitable, biologically inert thermoplastic polymer can be used in the junction members described herein. A preferred thermoplastic material is polyvinylacetate (PVA). The polymer also has the proper transition properties (e.g., temperature or current at which is becomes severable). Suitable detachment conditions are any conditions which allow for the safe, efficient, and reliable detachment of the implantable device from the delivery mechanism. Examples of such other thermoplastics that may be used singly or in combination include, but are not limited to, materials such as polyactide, polyglycolide, polyactide-co-glycolide polydioxanone, polyethylene, polyiminocarbonates, polycaprolactone, polyesters and the like. U.S. Pat. No. 5,292,321 to Lee discusses such suitable thermoplastic materials.

The thermoplastic junction member may take on a variety of thicknesses and coverage configurations depending upon a number of factors such as the type of implant, the degree of control over the release of the implantable device into the selected site desired by the user, the types and combinations of materials used, dimensional constraints of the catheter and sheath, and so forth. Typically, the diameter of the junction member is between about 0.1–0.5 mm and the length anywhere from about 1 to 10 mm. For all configurations, it is desired that the thermoplastic member have a thickness that will not prohibit the engaged junctions from freely moving within a catheter sheath or other associated equipment necessary to accomplish the desired objective of reliably and safely placing a implantable device at a selected site.

An energy source is connected to the junction member, for example via the delivery wire. The thermoplastic junction member is sufficiently melted and/or severed by application of a low-frequency energy or direct current, thereby detaching the implantable device from the delivery mechanism (e.g., wire). The low-frequency energy of DC does not adversely affect the subject and is typically between about 1 and 100 kHz, including any integer value therebetwen. Preferably, the low-frequency energy or direct current is below about 100 kHz, more preferably below about 80 kHz and even more preferably below about 50 kHz.

As noted above, the implantable member can be any suitable implantable device. The implant is desirably made up of a radiopaque, physiologically compatible material. For instance, the material may be platinum, gold, tungsten, or alloys of these. Certain polymers are also suitable for use in the implants, either alone or in conjunction with metallic markers providing radiopacity. These materials are chosen so that the procedure of locating the implant within the vessel may be viewed using radiography. However, it is also contemplated that the implantable device may be made of various other biologically inert polymers or of carbon fiber.

When the implantable member is a coil, its shape and constituent winding will depend upon the use to which the coil will be placed. For occluding peripheral or neural sites, the coils will typically be made of 0.05 to 0.15 mm diameter wire (platinum or platinum/tungsten alloy) that may be wound to have an inner diameter of 0.15 to 1.5 mm with a minimum pitch—that is to say that the pitch is equal to the diameter of the wire used in the coil. The outer diameter is then typically between 0.25 mm to 1.8 mm. The length of the coil will normally be in the range of 0.5 to 60 cm, preferably 0.5 to 40 cm. A discussion of this variation may be found, for example, in U.S. Pat. No. 4,994,069 to Ritchart et al.

Conventional catheter insertion and navigational techniques involving guidewires or flow-directed devices may be used to access the site with a catheter. Briefly, the implantable devices having polymeric detachable junctions described herein are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the mechanical devices which cause formation of an emboli and, at some later time, is at least partially replaced by neovascularized collagenous material formed around the implanted devices.

A selected site is reached through the vascular system using a collection of specifically chosen catheters and guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta.

A guidewire and neurovascular catheter such as that described in the Engelson patent are then placed through the guiding catheter as a unit. Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the assembly, for example including the implantable device at the distal end, is advanced through the catheter. The device is advanced past the distal end of the catheter so that it is free and positioned precisely at the desired treatment site.

The length of delivery mechanism will be such as to be capable of being advanced entirely through the catheter to place implantable device at the target site but yet with a sufficient portion of the distal end of the delivery mechanism protruding from the distal end of the catheter to enable detachment of the implantable device. For use in peripheral or neural surgeries, the delivery mechanism will normally about 100–200 cm in length, more normally 130–180 cm in length. The diameter of the delivery mechanism is usually in the range of 0.25 to about 0.90 mm.

Once the implantable device is at the selected site, low frequency energy or direct current is then supplied by the energy source and transmitted through the delivery mechanism to polymeric junction member so to sufficiently melt the thermoplastic polymer above its transition temperature until it is sufficiently softened or dissipated to free the junction member from the implantable device. Alternatively, a component that acts as a conductor (e.g., a conductive wire) can be inserted through the catheter alongside the delivery mechanism and the low frequency energy transmitted through it to melt the thermoplastic junction. In either case, following severing of the implantable device, the entire catheter may then be removed or the delivery mechanism may be withdrawn from the catheter lumen to provide for installation of other implantable devices. If additional implants are to be placed at the target site, the procedure is repeated. After the desired number of implants have been placed at the site, the catheter is withdrawn from the vessel.

Prior to the formation of assembly, it is desired to ensure that the thermoplastic material forming thermoplastic member coats substantially the entire surface of the junction member where it intersects both the implant and delivery mechanism junctions. This aids in electrically insulating the combination delivery mechanism-implantable device assembly. Electrical insulation helps to limit the heating effect of the energy, applied to soften the thermoplastic member, to the joined implantable device and delivery mechanism in the immediate vicinity of the thermoplastic member and to avoid excessive undesirable heating of the delivery mechanism and the implantable device. This concept is described in a different context in U.S. Pat. No. 5,743,905 to Eder et al., issued Apr. 28, 1998.

Alternatively, if it is desired to further protect the assembly from heating effects during detachment, an additional electrical insulating member may be affixed to the proximal section of delivery mechanism. If such an additional insulating member is used, it is desired, but not necessary, that it consist of an electrically insulating polymer material and/or thickness different from that of the thermoplastic member such that the thermoplastic member preferentially absorbs the energy applied during detachment by the energy source. The insulating material can be a polymer such as polyethylene, polypropylene, polyurethane, polyethylene terephthalate, polyvinylchloride, and is preferably a polymer from the class of polymers generally known as parylene. The insulation may be applied to the proximal end of delivery mechanism by a number of processes such as shrink-wrapping, dipping in molten polymer, spraying on in the form of a suspension or latex, or the like. The axial length of the additional insulating member and its thickness may vary depending upon the degree of additional electrical insulation desired, the specific configuration of the assembly, the application for which assembly is used, etc.

Modifications of the procedure and device described above, and the methods of using them in keeping with this invention will be apparent to those having skill in this mechanical and surgical art. These variations are intended to be within the scope of the claims that follow.

What is claimed is:

1. An assembly comprising:
   (a) an implantable device;
   (b) a deployment mechanism; and
   (c) a junction member comprising a thermoplastic polymer, wherein said junction member links the implantable device and deployment mechanism, wherein the junction member is detached from the implantable device by application of low-frequency energy less than 100 kHz.

2. The assembly of claim 1, wherein the thermoplastic polymer is PVA.

3. The assembly of claim 1, wherein the low frequency energy is less than 80 kHz.

4. The assembly of claim 1, wherein the deployment mechanism comprises a conductive wire.

5. The assembly of claim 1, wherein the implantable device comprises a vasoocclusive coil.

6. The assembly of claim 1, wherein the implantable device comprises a stent.

7. The assembly of claim 1, further comprising
   (d) a source of low frequency energy attached to the delivery mechanism.

8. The assembly of claim 1, further comprising:
   (d) a conductive member in operable contact with the junction member.

9. The assembly of claim 8, further comprising
   (e) a source of low frequency attached to the conductive member.

10. The assembly of claim 1, further comprising a catheter, said assembly being disposed within the catheter.

11. The assembly of claim 10, further comprising a negative electrode at the distal tip of the catheter.

12. A method of introducing an implantable device into a subject, the method comprising:
    (a) introducing an assembly according to claim 1 into the subject; and
    (b) detaching the implantable device by applying low frequency energy.

* * * * *